(12) United States Patent
Kang et al.

(10) Patent No.: US 7,570,737 B2
(45) Date of Patent: Aug. 4, 2009

(54) CARGO SECURITY INSPECTION METHOD AND SYSTEM BASED ON SPIRAL SCANNING

(75) Inventors: Kejun Kang, Beijing (CN); Li Zhang, Beijing (CN); Zhiqiang Chen, Beijing (CN); Haifeng Hu, Beijing (CN); Yuanjing Li, Beijing (CN); Yinong Liu, Beijing (CN); Guowei Zhang, Beijing (CN); Ziran Zhao, Beijing (CN); Yuxiang Xing, Beijing (CN); Yongshun Xiao, Beijing (CN)

(73) Assignees: Tsinghua University, Beijing (CN); Nuctech Company Limited, Beijing (CN)

(*) Notice: Subject to any disclaimer, the term of this patent is extended or adjusted under 35 U.S.C. 154(b) by 0 days.

(21) Appl. No.: 11/801,279

(22) Filed: May 8, 2007

(65) Prior Publication Data

US 2007/0280417 A1 Dec. 6, 2007

(30) Foreign Application Priority Data

May 8, 2006 (CN) .................. 2006 1 0076572

(51) Int. Cl.
*G01N 23/04* (2006.01)
(52) U.S. Cl. ................ 378/57; 378/15; 378/901
(58) Field of Classification Search ........... 378/4–20, 378/57, 58, 208, 901
See application file for complete search history.

(56) References Cited

U.S. PATENT DOCUMENTS

| | | | |
|---|---|---|---|
| 5,367,552 A | 11/1994 | Peschmann | |
| 5,796,802 A | 8/1998 | Gordon | |
| 5,901,119 A | 5/1999 | Inoue | |
| 6,343,109 B2 | 1/2002 | Doubrava et al. | |
| 6,788,761 B2 | 9/2004 | Bijjani et al. | |
| 7,113,569 B2 * | 9/2006 | Okumura et al. | 378/150 |
| 7,116,751 B2 * | 10/2006 | Ellenbogen et al. | 378/57 |
| 7,356,115 B2 * | 4/2008 | Ford et al. | 378/57 |
| 2005/0058242 A1 | 3/2005 | Peschmann | |
| 2005/0117700 A1 | 6/2005 | Peschmann | |
| 2005/0276376 A1 | 12/2005 | Eilbert | |

FOREIGN PATENT DOCUMENTS

| | | |
|---|---|---|
| DE | 31 50 306 A1 | 6/1983 |
| DE | 10 2004 031 130 A1 | 1/2006 |
| FR | 2 801 104 | 5/2001 |
| GB | 2 420 682 A | 5/2006 |
| WO | WO 2004/072685 | 8/2004 |
| WO | WO 2004/090576 A3 | 10/2004 |
| WO | WO 2005/119297 A3 | 12/2005 |

OTHER PUBLICATIONS

International Search Report in PCT/CN2007/001459, Aug. 9, 2007 (English Translation) 3 pages.

* cited by examiner

*Primary Examiner*—Jurie Yun
(74) *Attorney, Agent, or Firm*—Kenyon & Kenyon LLP

(57) ABSTRACT

A cargo security inspection method and system based on spiral scanning, the method including: spirally scanning an inspected object at a first precision to obtain the transmission projection data; judging whether there is a suspect area in the inspected area; scanning at least one slice of the suspect area at a second precision wherein the second precision is greater than the first precision; reconstructing a tomographic image of the at least one slice; and using the reconstructed tomographic image to judge whether there is any dangerous article in the suspect area.

22 Claims, 2 Drawing Sheets

CARGO SECURITY INSPECTION METHOD AND SYSTEM BASED ON SPIRAL SCANNING

FIELD OF THE INVENTION

The present invention relates to radiation detection technology, in particular, to a cargo security inspection method based on spiral scanning.

BACKGROUND INFORMATION

Security inspection is of great importance in fields such as anti-terrorism and fighting against trafficking in drugs and smuggling. After 9/11 terrorist attacks of the United States, people more and more emphasize security inspection of civil aviation. As the fighting against trafficking in drugs and smuggling is deepened, the requirement for inspection of aviation containers and luggage carried by railway becomes higher and higher.

At present, X-ray radiation imaging apparatuses are mostly used as security inspection apparatuses for use at airports, railway or highway transportation. Perspective imaging stands prominent in the art of radiation imaging. The biggest drawback of perspective imaging system lies in failure to solve the problem of overlapping of images of the object in the direction of rays and failure to achieve 3-dimensional inspection.

For example, if a plastic explosive is produced in the shape of thin sheets and sandwiched in a bulky object, when the thin sheets are parallel to the conveyance belt of the perspective imaging system, i.e., are disposed as being vertical to the X-ray sector, it is very difficult to observe presence of the thin sheets on the acquired images.

As technology develops, computed tomography (CT) imaging technology gradually becomes mature and has already been applied to luggage inspection systems. Inspecting luggage by a CT system requires rotational scanning and reconstructing a 3-dimensional image using the scanning data. In particular, as far as a spiral CT system is concerned, relative rotation and translation is carried out between a radiation source and an inspected object so that the radiation source has a spiral movement trajectory relative to the inspected object. In the prior art spiral CT systems, a radiation source moves spirally relative to the inspected object with a small pitch so as to obtain scanning data (i.e., high-precision scanning data or complete scanning data) of all slices of the inspected object. As a result, the inspection speed of such a spiral CT system is generally very slow so that a great deal of time is spent in a conventional inspection. However, at present security inspection systems in aviation, railway or highway transportation generally requires on-line full-time inspection and articles need to be quickly inspected. Very apparently, the scanning speed of the prior art spiral CT systems cannot meet the requirement for inspection speed. Certainly, increase of the scanning pitch of the spiral CT system will improve the scanning speed and thereby improve the inspection speed. However, increase of the pitch will reduce scanning precision and thereby reduces precision of the reconstructed 3-dimensional image and thereby reduces accuracy in inspection of cargo.

SUMMARY OF THE INVENTION

In view of the above drawbacks in the prior art, an object of the present invention is to provide a cargo security inspection method based on spiral scanning to save security inspection time and realize quick and accurate inspection of cargo.

To achieve the above object, the technical solution of the present invention is fulfilled as follows.

An embodiment of the present invention provides a cargo security inspection method based on spirally scanning for inspecting an inspected object by a cargo security inspection system, the cargo security inspection system comprising a radiation source for generating ray beams and a data collecting unit for collecting transmission projection data of ray beams having transmitted through the inspected object. The method comprises:

Step A: spirally scanning the inspected object at a first precision using a ray beam, and the data collecting unit obtaining the transmission projection data of the ray beam transmitting through the inspected object;

Step B: judging whether there is a suspect area in an inspected area according to the transmission projection data, performing Step C if there is a suspect area, and, it not, ending the inspection;

Step C: scanning at least one slice of said suspect area at a second precision using the ray beam, the data collecting unit acquiring transmission projection data of the ray beam transmitting through said at least one slice, wherein the second precision is greater than the first precision in Step A; and Step D: reconstructing a tomographic image of said at least one slice using the transmission projection data obtained in Step C, and using the reconstructed tomographic image to judge whether there is any dangerous article in the suspect area.

Preferably, in Step A, the scanning trajectory of the ray beam on the inspected object is a spiral trajectory about the inspected object, the pitch of the spiral trajectory being in the range of 5-10.

Preferably, the cargo security inspection system further comprises a carrier for carrying the inspected object, wherein in Step A, said carrier rotates and said inspected object rotates along with said carrier in a rotation plane; and furthermore, said ray beam and said data collecting unit synchronously translate in a direction perpendicular to the rotation plane of the inspected object.

Preferably, said Step B includes: processing the transmission projection data using a dangerous article inspection algorithm and searching a suspect area from the transmission projection data. Alternatively, said Step B preferably includes: using the transmission projection data to reconstruct a 3-dimensional image of the inspected object and using said 3-dimensional image to search any suspect area. Alternatively, said Step B preferably includes: processing the transmission projection data using dangerous article inspection algorithm and searching a suspect area from the transmission projection data, then using the transmission projection data in this suspect area to reconstruct a 3-dimensional image of the suspect area, thereby eliminating suspicion to the suspect area or maintaining suspicion to the suspect area according to the 3-dimensional image of the suspect area.

Preferably, said 3-dimensional image is a physical parameter distribution image about at least one physical parameter. Preferably, the physical parameter distribution image is reconstructed using a CT reconstruction algorithm.

Preferably, the radiation source is a single energy radiation source or a dual energy radiation source. Preferably, when the radiation source is the single energy radiation source which generates a single energy ray beam, said at least one physical parameter is the attenuation coefficient of the inspected object at the ray energy. Preferably, when the radiation source is the dual energy radiation source which generates a ray beam having a first energy and a ray beam having a second energy that is different than the first energy, said at least one physical parameter includes at least one of atomic number, electron density, the attenuation coefficient of the inspected object at the first energy, and the attenuation coefficient of the inspected object at the second energy.

Preferably, in Step D, said tomographic image is a physical parameter distribution image about at least one physical parameter of the slice. Preferably, the physical parameter distribution image of the slice is reconstructed using a CT reconstruction algorithm.

Preferably, in Step C, the ray beam scans each individual slice of said at least one slice in a closed circular trajectory.

Preferably, in Step C, said at least one slice is a plurality of slices in the suspect area. Preferably, in Step C, the ray beam carries out spirally scanning of said plurality of slices in a spiral trajectory. Preferably, Step D further comprises combining tomographic images of the plurality of slices into one 3-dimensional image, and judging whether there is any dangerous article in the suspect area according to the 3-dimensional image.

Preferably, the method further comprises displaying the tomographic image and/or the 3-dimensional image.

The basic idea of the present invention is described as follows. In the present invention, an object is inspected by a "two-step" method. The first step of the "two-step" method can be called "rough inspection" which exhibits a lower precision and aims to seek for any potential suspect area of dangerous articles in the inspected object. The second step of the "two-step" method can be "fine inspection" which exhibits a higher precision and aims to confirm whether there is really a dangerous article in the suspect area.

As for the "rough inspection," spirally scanning is done to the inspected object with a first precision. The first precision is less than the precision of the conventional spiral CT scanning. Therefore, compared with the conventional spiral CT scanning, what the rough inspection gets is low-precision scanning data or incomplete scanning data. However, since the only purpose of the rough inspection is to seek for a suspect area of a potential dangerous article, such low-precision scanning data or incomplete scanning data are already sufficient. Furthermore, since the rough inspection is carried out at a low precision, the scanning speed thereof can be relatively fast and thereby save the inspecting time, compared with the conventional spiral CT scanning. The scanning precision can be indicated by a scanning pitch. For example, as for the conventional spiral CT scanning, its scanning pitch is usually in the range of 0.5-1.0, whereas in rough inspection of the present invention, the scanning pitch can be in the range of 5-10 (the value of pitch herein is a relative pitch), so the scanning speed is obviously faster.

As for the "fine inspection," spiral scanning is done to the inspected object with a second precision. Since the aim of the fine inspection is to confirm whether there is really a dangerous article in the suspect area, the second precision is greater than the first precision of the rough inspection. For example, the second precision can be substantially the same as the conventional CT scanning or spiral CT scanning so as to obtain high-precision scanning data or substantially complete scanning data. For example, the fine inspection can utilize a circular trajectory scanning or small-pitch spiral scanning (e.g., a pitch in the above range of 0.5-1.0).

The advantageous effects of the present invention are as follows.

1. As compared with the whole scanning and reconstruction of the inspected object, the method according to the present invention substantially shortens the time for scanning the inspected object and thereby saves cargo security inspection time and realize quick and accurate inspection of cargo because the inspected object is first quickly spirally scanned at a low precision and then a high-precision computed tomographic scanning is effected only to the suspect area.

2. As compared with conventional perspective imaging of the inspected object, the present invention carries out computed tomographic scanning of the suspect area and reconstructs a tomographic image of the suspect area, so dangerous articles such as plastic explosive purposefully hidden in the luggage can be found and the problem of overlapping of the objects in the perspective image can be efficiently solved according to the method of the present invention.

3. The present invention does not require any change of hardware based on the prior art cargo security inspection system, so the costs are low and the present invention can be easily spread and applied extensively.

DETAILED DESCRIPTION

The present invention will be described in detail with reference to embodiments and accompanying drawings to make the technical solution of the present invention clearer.

Figure 1:
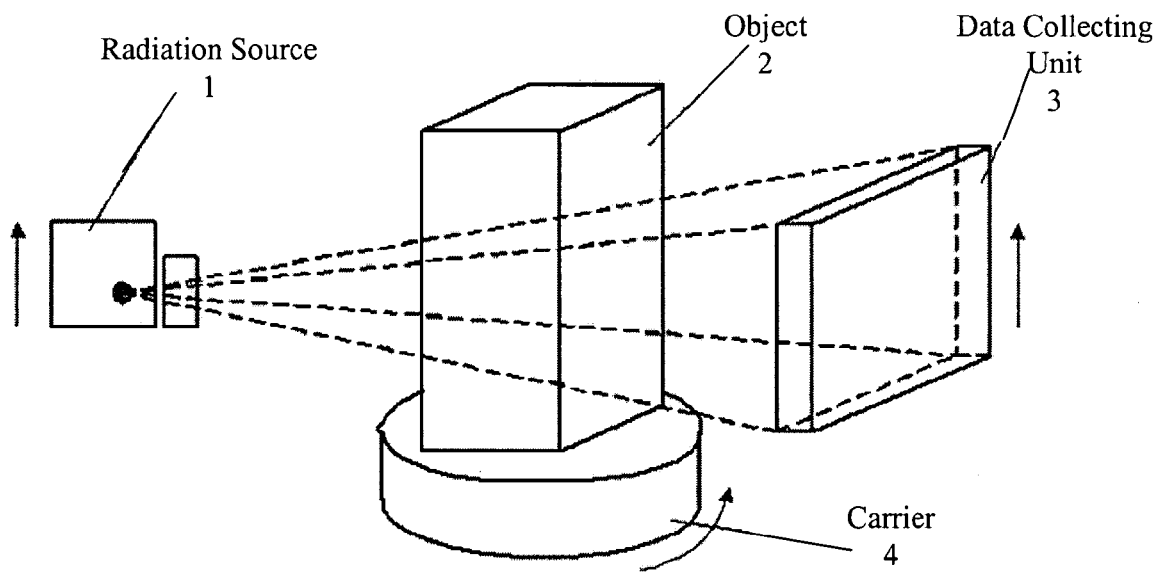
FIG. 1 is a diagram showing the structure of a conventional cargo security inspection system for realizing the present invention.

FIG. 1 shows an exemplary cargo security inspection system for realizing the method according to the present invention, comprising a radiation source 1, a carrier 4, a data collecting unit 3 and a main control and data processing computer (not shown).

The radiation source 1 can be a single energy radiation source or a dual energy radiation source, e.g., X-ray accelerator or isotope source. As far as the single energy radiation source is concerned, it generally generates ray beams with energy of 6 Mev. Using the single energy radiation source, the attenuation coefficient of the object can be obtained in a scanning process. As far as dual energy ray beams, they can generate ray beams with two kinds of energy at a very high frequency and in an alternative manner, i.e., a first energy ray beam and a second energy ray beam. In general, the first energy ray beam is 3 Mev, and the second energy ray beam is 6 Mev. Using the dual energy radiation source, physical parameters of the object, such as atomic number, electron density, the attenuation coefficient at the first energy ray beam and the attennuation coefficeint at the second energy ray beam, can be obtained in a scanning process. The dual energy radiation source is preferable, and using the above physical parameters it obtains, cargo security inspection rate can be improved, erroneous reporting ratio of cargo security inspection can be reduced, and speed and reliability of cargo security inspection can be substantially improved.

The carrier 4 can rotate in the horizontal direction and is used to carry an inspected object 2. The inspected object 2 is secured to the carrier 4 and will not displace relative to the carrier 4.

The data collecting unit 3 is generally a detector array located opposite the radiation source 1. The central ray of the cone beam generated by the radiation source 1 transmits through the center of the detector array, and the range of the cone beam right covers the surface of the whole detector array.

To fulfill quick and precise inspection, the data collecting unit 3 further comprises means for precisely measuring or calibrating the following system parameters: a distance from the radiation source to the center of the carrier, a distance from the radiation source to the center of the detector, a rotational speed of the carrier, vertical movement speed of the radiation source and the detector, ray beam energy, sampling interval of the detector, physical dimension of the detectors, and the like. The physical dimension of the detectors comprises the physical dimension of an individual detector element and physical dimension of the detector array. Means for measuring or calibrating said system parameters are known in the art, and will not be described in detail herein.

The main control and data processing computer comprises a scan control unit and data processing. It can be a single computer or a computer group or work station comprised of a plurality of computers. The computer is generally a high-performance PC. The scan control unit can control uniform-speed rotation of the carrier 4 and control synchronous movement of the radiation source 1 and the detector array 3 in a vertical direction.

Before the inspection, the inspected object 2 is first disposed on the horizontal carrier 4. The inspected object 2 can be moved onto the carrier 4 via a conveyance belt or a roller conveyor. Besides, to ensure the inspected object 2 does not move relative to the carrier 4 during inspection, the surface where the carrier 4 contacts the inspected object 2 is made as a coarse surface or a fixing means is additionally provided.

Upon completion of the above preparation work, the whole cargo security inspection system is started so as to perform security inspection of the inspected object.

Figure 2:
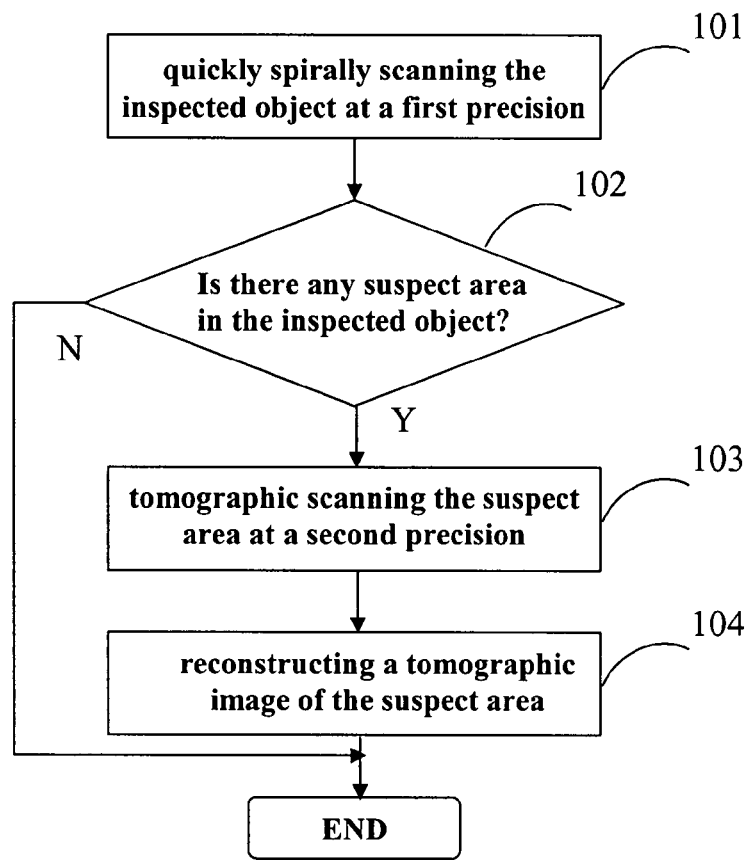
FIG. 2 is a flowchart illustrating a procedure for fulfilling the overall technical solution of the cargo security inspection according to the present invention.

FIG. 2 shows a procedure diagram for fulfilling the technical solution of the cargo security inspection method according to the present invention. As shown in FIG. 2, in Step 101, the inspected object is quickly spirally scanned at a first precision to obtain transmission projection data. Step 102 relates to judging whether there is a suspect area in the inspected object: if there is a suspect area, Step 103 is performed; if not, the procedure is ended; Step 103 relates to effecting tomographic scanning to the suspect area at a second precision, wherein the second precision is higher than the first precision; and Step 104 relates to reconstructing a tomographic image of the suspect area.

In Step 101, the single energy or dual energy ray beam effects quick and spiral scanning of the inspected object at the first precision, and the data collecting unit obtains the transmission projection data of the ray beam transmitting through the inspected object. Upon performing Step 101, the cargo security inspection system is started, the main control and data processing computer controls the carrier to carry the inspected object for rotation at a uniform speed. The radiation source and the data collecting unit synchronously move in a vertical direction, and meanwhile the ray beam generated by the radiation source transmits through the inspected object carried by the carrier, and the data collecting unit receives the transmission projection data having transmitted through the inspected object. The scanning trajectory of the ray beam on the inspected object is a spiral trajectory about the inspected object. In Step 101, the first precision refers to a precision smaller than the precision of a conventional spiral CT scanning. For example, in one embodiment, the pitch of the spiral trajectory is in the range of 5-10, which is apparently greater than the pitch 0.5-1.0 of the conventional spiral CT scanning. During the spiral scanning, location information in the scanning area and the collected transmission projection data are constantly transferred to the main control and data processing computer.

In Step 102, judgement is made on whether there is a suspect area in the inspected area according to the transmission projection data obtained from Step 101. There are the following three manners for judging whether there is a suspect area.

1) Processing the transmission projection data using a known dangerous article inspection algorithm and searching a suspect area from the transmission projection data. The main control and data processing computer carries out the dangerous article inspection algorithm to search a potential suspect area of dangerous articles from the projection data. If there is a suspect area, the location of the suspect area is marked.

2) The main control and data processing computer uses these transmission projection data to reconstruct a 3-dimensional image of the inspected object and use the 3-dimensional image to search a suspect area. If there is a suspect area, the location of the suspect area is marked. Compared with the first manner, this manner is more reliable.

3) This manner is a combination of the first and second manners. First of all, the transmission projection data is processed using the dangerous article inspection algorithm and searching a suspect area from the transmission projection data, and then, using the transmission projection data in this suspect area, a 3-dimensional image of the suspect area is reconstructed, eliminating suspicion to the suspect area or maintaining suspicion of the suspect area according to the 3-dimensional image of the suspect area. This manner is preferable, particularly when the first manner is not sufficient to definitely confirm the suspect area.

In the above second and third manners, the reconstructed 3-dimensional image of the inspected object and the reconstructed 3-dimensional image of this suspect area are physical parameter distribution images about at least one physical parameter. The physical parameter herein is related to the type of radiation source. As above described, when the radiation source is a single energy radiation source, the physical parameter is the attenuation coefficient of the inspected object. When the radiation source is a dual energy radiation source, the physical parameter includes one or more of atomic number, electron density, the attenuation coefficient of the inspected object at the first energy, and the attenuation coefficient of the inspected object at the second energy. A 3-dimensional image can be reconstructed with respect to each physical parameter. When this 3-dimensional image is reconstructed, the data collecting unit transfers the transmission projection data to the main control and data processing computer, and the main control and data processing computer reconstructs these transmission projection data as a physical parameter distribution image using CT reconstruction algorithm. When the radiation source is a dual energy radiation source, the 3-dimensional image is reconstructed using dual energy CT reconstruction algorithm.

Upon performing Step 102, the data collecting unit transfers the transmission projection data to the main control and data processing computer. It is the main control and data processing computer that judges whether there is any suspect area in the inspected object according to one of the above three manners.

Particularly, Step 101 and Step 102 can be synchronously carried out, that is, judging whether there is any suspect area of dangerous articles immediately after completion of scanning. The cargo security inspection systems carries out quick and spiral scanning of the whole inspected object: when scanning reaches the top of the inspected object from bottom of the inspected object, the carrier 4 stops rotating, the dual energy radiation source 1 and the detector array 3 stop rising and working, and the main control and data processing computer displays whether there is a suspect area.

If no suspect area is found in Step 102, the inspected object will be moved away via a conveyance means, and all parts of the system return to their original places for next inspection. If a suspect area is found in Step 102, Step 103 will be carried out.

In Step 103, scanning is effected to at least one slice of said suspect area using a ray beam with a second precision, and the data collecting units acquires transmission projection data of the ray beam transmitting through said at least one slice. The second precision is greater than the first precision in Step 101. For example, the second precision is substantially identical with the precision of conventional CT scanning or spiral CT scanning. Said at least one slice can be one or more typical slices in the suspect area, and these slices can be spatially continuous or discontinuous. Since in Step 103 scanning is conducted only to the suspect area, the time used for scanning is obviously less than the time used in conventional CT scanning or spiral CT scanning of the whole inspected object.

Upon performing Step 103, the ray beam can respectively scan all the slices in a closed circular trajectory. In this case, the radiation source and the data collecting unit move synchronously in the vertical direction and stop after reaching the vertical position of the slice to be inspected, the main control and data processing computer controls the carrier to carry the inspected object for rotation at a uniform speed. The ray source generates ray beams to transmit through the slice, and the data collecting unit receives the transmission projection data. If a plurality of slices of the suspect area are scanned, the above scanning procedure can be repeated.

When Step 103 is carried out, if there are a plurality of slices in the suspect area needing to be scanned and these slices are spatially continuous, the ray beam carries out spiral scanning of said plurality of slices in a spiral trajectory. In this case, the radiation source and the data collecting unit move synchronously in a vertical direction to a vertical position where the lowermost one of said plurality of slices is located. Then, the main control and data processing computer controls the carrier to carry the inspected object for rotation at a uniform speed, and the radiation source and the data collecting unit moves upwardly synchronously in a vertical direction up to the topmost one of said plurality of slices. During this procedure, the ray source generates ray beams to transmit through these slices, and the data collecting unit receives the transmission projection data. In this case, the spiral scanning is substantially the same as the conventional spiral CT scanning. For example, the pitch of the spiral scanning can be in the range of 0.5-1.0.

In Step 104, a tomographic image of each of the slices is reconstructed using the transmission projection data obtained in Step 103, and the reconstructed tomographic image is used to judge whether there is any dangerous article in the suspect area. The tomographic image can be a physical parameter distribution image regarding the physical parameter of the slice. Herein, the relation of the physical parameter and the radiation source type are the same as the above related content. No detailed description will be given herein. In Step 104, the data collecting unit transfers the transmission projection data of the slices to the main control and data processing computer, and the main control and data processing computer reconstructs these transmission projection data as a physical parameter distribution image using CT reconstruction algorithm. When the radiation source is a dual energy radiation source, tomographic images of all slices are reconstructed using dual energy CT reconstruction algorithm. When these slices are spatially continuous, a plurality of tomographic images can be combined into one 3-dimensional image, and the 3-dimensional image is used to judge whether there is any dangerous article in the suspect area. The main control and data processing computer can display the tomographic image and/or the 3-dimensional image for observation of a security inspector.

After Step 104, if the suspect area is judged as having no dangerous article, a conveyance means is used to carry away the inspected object and the cargo security inspection system will return in place for the coming next inspection.

If the suspicion of dangerous article in the suspect area cannot be eliminated yet after Step 104, the inspected object can be further sent to the security inspector for confirmation by manual inspection, and the cargo security inspection system will return in place for the coming next inspection.

In the cargo security inspection system according to the present invention, range of the dangerous articles and alarming threshold of various dangerous articles need to be predetermined, which needs consultation with aviation and related sectors and which are likely to be adjusted as the inspection environment changes and security ratings vary.

Figure 3:
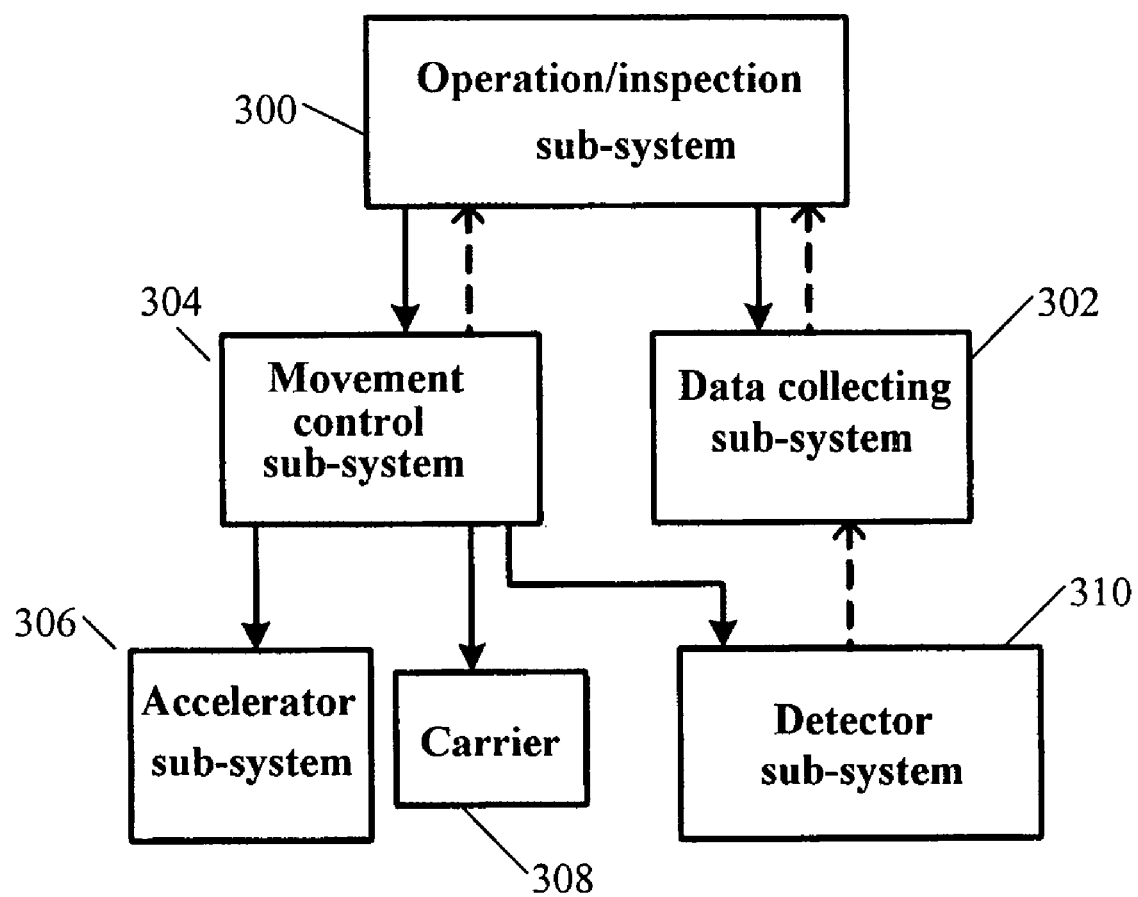
FIG. 3 is a diagram showing control signals and data flow direction of the cargo security inspection system according to the present invention.

In the whole inspection system, mechanical and electrical control, data transmission, image reconstruction, data processing and automatic inspection of dangerous articles are all performed by computers. Control signals and data flow direction of the system are shown in FIG. 3, wherein solid lines denote control signals and dotted line denote data information.

Operation/inspection sub-system software 300 is operated at a workstation to obtain projection data from a data collecting sub-system 302 and positional information from a movement control sub-system 304, and to execute the dangerous article automatic inspection algorithm to give a judgment result and send out a control command for control of an accelerator sub-system 306, a carrier 308, and/or a detector sub-system 310. Various images can be displayed on a display for checking and operation of a security inspector. If necessary, the security inspector can manually operate on the computer to assist the inspection algorithm in carrying out dangerous article inspection.

The above are only embodiments of the present invention and not used to limit the present invention. According to the contents disclosed in the present invention, a person having ordinary skill in the art can apparently think of some identical, alternative solutions which should all be included in the protection scope of the present invention.

What is claimed is:

1. A cargo security inspection method using a security inspection system configured to perform spiral scanning for inspecting an inspected object, the cargo security inspection system comprising a radiation source for generating ray beams and a data collecting unit for collecting transmission projection data of the ray beams having transmitted through the inspected object, the method comprising:

in step A:
spirally scanning the inspected object at a first precision using a ray beam to transmit through the inspected object; and
the data collecting unit obtaining a first transmission projection data of the ray beam transmitting through the inspected object;

in step B, judging whether there is a suspect area in an inspected area according to the first transmission projection data, step C being performed conditional upon that the suspect area is judged to exist, and the inspection otherwise ending;

in step C:
scanning at least one slice of the suspect area at a second precision using the ray beam to transmit through the at least one slice; and
the data collecting unit acquiring a second transmission projection data of the ray beam transmitting through the at least one slice, wherein the second precision is greater than the first precision; and in step D, constructing a tomographic image of the at least one slice using the second transmission projection data obtained in step C;

wherein:
in step A, a scanning trajectory of the ray beam on the inspected object is a spiral trajectory about the inspected object;
the first precision is at a first pitch;
the second precision is at a second pitch; and
the first pitch is in the range of 5-10 relative pitch, and is substantially larger than the second pitch, resulting in an incomplete CT scanning in step A.

2. The method according to claim 1, wherein:
the cargo security inspection system further comprises a carrier for carrying the inspected object;
in step A, the carrier rotates and the inspected object rotates along with the carrier in a rotation plane; and
the ray beam and the data collecting unit synchronously translate in a direction perpendicular to the rotation plane of the inspected object.

3. The method according to claim 1, further comprising:
in step B, processing the first transmission projection data using a dangerous article inspection algorithm, wherein the judging of step B is performed using the first transmission projection data.

4. The method according to claim 1, further comprising:
in step B, constructing a 3-dimensional image of the inspected object using the first transmission projection data, wherein the judging of step B is performed using the 3-dimensional image.

5. The method according to claim 4, wherein the 3-dimensional image is a physical parameter distribution image about at least one physical parameter.

6. The method according to claim 5, wherein the physical parameter distribution image is constructed using a CT reconstruction algorithm.

7. The method according to claim 6, wherein the radiation source is a single energy radiation source which generates a single energy ray beam, and said at least one physical parameter is an attenuation coefficient of the inspected object at the single energy.

8. The method according to claim 6, wherein the radiation source is a dual energy radiation source which generates a ray beam having a first energy and a ray beam having a second energy that is different than the first energy, and said at least one physical parameter includes at least one of atomic number, electron density, an attenuation coefficient of the inspected object at the first energy, and an attenuation coefficient of the inspected object at the second energy.

9. The method according to claim 1, wherein the judging of step B includes:
searching for the suspect area using the first transmission projection data by a dangerous article inspection algorithm; and if the suspect area is found:
constructing a 3-dimensional image of the suspect area after the suspect area is found using a portion of the first transmission projection data corresponding to the suspect area; and
analyzing the 3-dimensional image of the suspect area to determine whether the suspect area is to maintain its suspicious status.

10. The method according to claim 1, wherein the radiation source is one of a single energy radiation source and a dual energy radiation source.

11. The method according to claim 1, wherein, the tomographic image is a physical parameter distribution image about at least one physical parameter of the at least one slice.

12. The method according to claim 11, wherein the physical parameter distribution image of the at least one slice is constructed using a CT reconstruction algorithm.

13. The method according to claim 11, wherein the radiation source is a single energy radiation source which generates a single energy ray beam, and the at least one physical parameter is an attenuation coefficient of the inspected object at the single energy.

14. The method according to claim 11, wherein the radiation source is a dual energy radiation source which generates a ray beam having a first energy and a ray beam having a second energy that is different than the first energy, and the at least one physical parameter includes at least one of atomic number, electron density, an attenuation coefficient of the inspected object at the first energy, and an attenuation coefficient of the inspected object at the second energy.

15. The method according to claim 1, wherein, in step C, the ray beam scans each one of the at least one slice in a closed circular trajectory.

16. The method according to claim 1, further comprising:
in step D, judging whether there is any dangerous article in the suspect area using the constructed tomographic image.

17. The method according to claim 16, wherein, in step C, the at least one slice is a plurality of slices in the suspect area.

18. The method according to claim 17, wherein, in step C, the plurality of slices are spirally scanned in a spiral trajectory using the ray beam.

19. The method according to claim 17, further comprising:
in step D, combining respective tomographic images of the plurality of slices into one 3-dimensional image;
wherein the judging of step D is performed according to the 3-dimensional image.

20. The method according to claim 19, further comprising:
displaying at least one of (a) at least one of the tomographic images and (b) the 3-dimensional image.

21. The method of claim 16, wherein the judging of step D is performed using a dangerous article inspection algorithm.

22. A cargo security inspection system for inspecting an inspected object, the cargo security inspection system comprising:
a radiation source for generating ray beams;
a data collecting unit for collecting transmission projection data of the ray beams having been transmitted through the inspected object; and
an inspection arrangement configured to perform an inspection, the inspection arrangement comprising:
a first arrangement configured to spirally scan the inspected object at a first precision using one of the ray beams to transmit through the inspected object towards the data collecting unit for the data collecting unit to collect a first transmission projection data of the ray beam;

a second arrangement configured to judge whether there is a suspect area in an inspected area according to the first transmission projection data;

a third arrangement configured to scan at least one slice of the suspect area at a second precision using the ray beam to transmit through the at least one slice towards the data collecting unit for the data collecting unit to collect a second transmission projection data of the ray beam, wherein the second precision is greater than the first precision; and a fourth arrangement configured to construct a tomographic image of the at least one slice using the second transmission projection data;

wherein the inspection arrangement is configured such that:

a scanning trajectory on the inspected object of the one of the ray beams used by the first arrangement is a spiral trajectory about the inspected object;

the third arrangement scans the at least one slice and the fourth arrangement constructs the tomographic image conditional upon that the suspect area is judged by the second arrangement to exist, the inspection arrangement configured to otherwise end the inspection in response to the second arrangement failure to judge that the suspect area exists;

the first precision is at a first pitch;

the second precision is at a second pitch; and the first pitch is in the range of 5-10 relative pitch, and is substantially larger than the second pitch, resulting in an incomplete CT scanning by the first arrangement.

* * * * *